US012673055B2

(12) United States Patent
Polymeropoulos et al.

(10) Patent No.: US 12,673,055 B2
(45) Date of Patent: Jul. 7, 2026

(54) TREATMENT OF ATOPIC DERMATITIS WITH TRADIPITANT

(71) Applicant: Vanda Pharmaceuticals Inc., Washington, DC (US)

(72) Inventors: Mihael H. Polymeropoulos, Potomac, MD (US); Gunther Birznieks, Chevy Chase, MD (US); Christos Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 863 days.

(21) Appl. No.: 17/760,239

(22) PCT Filed: Feb. 24, 2021

(86) PCT No.: PCT/US2021/019376
§ 371 (c)(1),
(2) Date: Aug. 5, 2022

(87) PCT Pub. No.: WO2021/173641
PCT Pub. Date: Sep. 2, 2021

(65) Prior Publication Data
US 2023/0226046 A1 Jul. 20, 2023

Related U.S. Application Data

(60) Provisional application No. 62/981,481, filed on Feb. 25, 2020.

(51) Int. Cl.
*A61K 31/497* (2006.01)
*A61P 17/04* (2006.01)

(52) U.S. Cl.
CPC ............ *A61K 31/497* (2013.01); *A61P 17/04* (2018.01)

(58) Field of Classification Search
CPC .............. A61K 31/4035; A61K 31/438; A61K 31/439; A61K 31/444; A61K 31/454;
(Continued)

(56) References Cited

U.S. PATENT DOCUMENTS 5,585,385 A 12/1996 Natsugari et al.
6,329,394 B1 12/2001 Hagan et al.
(Continued)

FOREIGN PATENT DOCUMENTS

JP 2004250329 A 9/2004
JP 2006199614 A 8/2006
(Continued)

OTHER PUBLICATIONS

Anonymous, "Vanda Reports results from the EPIONE study of Tradipitant in the treatment of Pruritus in Atopic Dermatitis," Cision PR Newswire, Feb. 25, 2020, XP055800178, 7 pages.
(Continued)

*Primary Examiner* — Savitha M Rao
(74) *Attorney, Agent, or Firm* — Hoffman Warnick LLC

(57) ABSTRACT

The disclosure relates generally to improvements in the treatment of pruritus, atopic dermatitis (AD), and associated symptoms with tradipitant. More particularly, it relates to a method for increasing the likelihood of achieving optimal therapeutic response in the treatment of an AD patient, where the AD patient is one for whom a potential therapy of choice may include the administration of an amount of an NK-1 antagonist, e.g. tradipitant effective to treat the patient's AD.

20 Claims, 4 Drawing Sheets

(58) Field of Classification Search
CPC .. A61K 31/495; A61K 31/496; A61K 31/497; A61K 31/675; A61P 17/04
See application file for complete search history.

(56) References Cited

U.S. PATENT DOCUMENTS

| | | | | |
|---|---|---|---|---|
| 7,179,804 | B2 | 2/2007 | Amegadzie et al. | |
| 7,320,994 | B2 | 1/2008 | Amegadzie et al. | |
| 7,381,826 | B2 | 6/2008 | Borghese et al. | |
| 7,799,782 | B2 | 9/2010 | Munson et al. | |
| 8,772,496 | B2 | 7/2014 | Chen | |
| 10,463,655 | B2 | 11/2019 | Polymeropoulos et al. | |
| 10,772,880 | B2 | 9/2020 | Polymeropoulos et al. | |
| 10,821,099 | B2 | 11/2020 | Polymeropoulos | |
| 11,324,735 | B2 | 5/2022 | Polymeropoulos et al. | |
| 11,549,147 | B2 | 1/2023 | Polymeropoulos et al. | |
| 2019/0216779 | A1 | 7/2019 | Basta et al. | |
| 2020/0197379 | A1 * | 6/2020 | Choi | A61K 47/26 |

FOREIGN PATENT DOCUMENTS

| | | | |
|---|---|---|---|
| JP | 2008530522 | A | 8/2008 |
| JP | 2014193155 | A | 10/2014 |
| RU | 2724053 | C2 | 6/2019 |
| WO | 2007096782 | A2 | 8/2007 |
| WO | 2014209962 | A1 | 12/2014 |
| WO | 2016195723 | A1 | 8/2016 |
| WO | 2017060488 | A1 | 4/2017 |
| WO | 2019/055225 | A1 | 3/2019 |
| WO | 2020/023879 | A1 | 1/2020 |
| WO | 2020/023898 | A1 | 1/2020 |

OTHER PUBLICATIONS

Eichenfield et al., "Guidelines of care for the management of atopic dermatitis, Section 1. Diagnosis and assessment of atopic dermatitis," J. Am. Acad. Dermatol., 70:338-351, Feb. 2014, 14 pages.
Futamura et al., "A systematic review of Investigator Global Assessment (IGA) in atopic dermatitis (AD) trials: Many options, no standards," J. Am. Acad. Dermatol., 74:288-294, Feb. 2016 (online Dec. 11, 2015), XP029385856, 7 pages.
International Search Report and Written Opinion, International Application No. PCT/US2021/019376, dated May 18, 2021,16 pages.
Sidbury et al., "Guidelines of care for the management of atopic dermatitis, Section 3. Management and treatment with phototheraphy and systemic agents," J. Am. Acad. Dermatol., 71:327-349, Aug. 2014, 23 pages.
Smieszek et al., "Correlation of age-of-onset of Atopic Dermatitis with Filaggrin loss-of-function variant status," Scientific Reports, 10:2721, 2020, 11 pages.
Smieszek et al., "Letter Genomic and phenotypic characterization of Investigator Global Assessment (IGA) scale-based endotypes in atopic dermatitis," J. Am. Acad. Dermatol., Jan. 7, 2021, XP055800349, 3 pages.
Welsh et al., "Neurokinin-1 receptor antagonist tradipitant improves itch associated with mild atopic dermatitis: 3 Results from EPIONE a randomized clinical trial," medRxiv, Jun. 24, 2020, XP055800177, 17 pages.
Hagiwara, D. "Discovery of Low-Molecular Weight Antagonists of Substance P: Recent Developments and Prospects as a Therapeutic Agent," Journal of Synthetic Organic Chemistry (Japan), vol. 52, Issue 5, 1994, pp. 445-452.
Shinya Usui, Decision of Refusal, Japanese Patent Application No. 2021-012356 "Method of Treatment with Tradipitant", pp. 1-3 (Sep. 20, 2022).
Trower et al., "Neurokinin-1 receptor antagonist orvepitant is an effective inhibitor of itch-associated response in a Mongolian gerbil model of scratching behaviour," Experimental Dermatology, 2014: 23, pp. 853-864.
Santini et al., "Aprepitant for management of severe pruritus related to biological cancer treatments: a pilot study," The Lancet, vol. 13; Oct. 2012; Published online Sep. 18, 2012 pp. 1020-1024.
FDA; "Guidence for Industry Exposure-Response Relationships—Study Design, Data Analysis, and Regulatory Applications;" Published Apr. 2003; pp. 1-28.
Sun et al., "Particle Size Specifications for Solid Oral Dosage Forms: A Regulatory Perspective;" American Pharmaceutical Review, Published May 1, 2010; pp. 1-9.
Sadick Research Group; "Tradipitant in Treatment-Resistant Pruritus Associated With Atopic Dermatitis;" ClinicalTrials.gov Identifier NCT02672410; First Received Feb. 1, 2016; last Updated Feb. 2, 2016; accessed on Feb. 11, 2016; pp. 3; <https://clinicaltrials.gov/ct2/show/study/NCT02672410?TERM=TRADIPITANT&RANK=3>.
George et al., "Supporting Online Material for Neurokinin 1 Receptor Antagonism as a Possible Therapy for Alcoholism," Science, vol. 319, No. 2869, dated Mar. 14, 2008, 14 pages.
George et al., "Neurokinin 1 Receptor Antagonism as a Possible Therapy for Alcholism;" Science, vol. 319, No. 2869, dated Mar. 14, 2008, 6 pages.
Stander et al., "Targeting the Neurokinin Receptor 1 with Aprepitant: A Novel Antipruritic Strategy," PLOS ONE, vol. 6., No. 6, Jan. 1, 2010, 6 pages.
Tauscher et al., "Development of the 2nd generation neurokinin-1 receptor antagonist LY686017 for social anxiety disorder;" European Neuropsychopharmacology; 2010; Elsevier Science Publishers BV, Amsterdam, NL, vol. 20, No. 2, Feb. 1, 2010, 8 pages.
Anonymous, "History of Changes for Study: NCT02004041: Proof of Concept of VLY-686 in Subjects With Treatment-Resistant Pruritus Associated with Atopic Dermatitis," U.S. National Library of Medicine, ClinicalTrials.gov archive, retrieved from: https://clinicaltrials.gov/ct2/history/NCT02004041?A=4&B=4&C=merged on Dec. 16, 2019, 9 pages.
Anonymous, "History of Changes for Study: NCT01919944: Study of Itch Control by VLY-686 in Healthy Volunteers After Intradermal Injections of Substance P," U.S. National Library of Medicine, ClinicalTrials.gov archive, retrieved from: https://clinicaltrials.gov/ct2/history/NCT01919944?A=5&B=5&C=merged on Dec. 16, 2019, 9 pages.
Stander et al., "An Investigational Study of Tradipitant for the Treatment of Chronic Pruritus in Patients With Atopic Dermatitis," Acta Dermato-Venereologica 2015 Medical Journals/ACTA D-V NLD; vol. 95; No. 7; 2015; XP002786610; ISSN: 1651-2057; Abstract.
Mittermann et al., "IgE Sensitization Profiles Differ between Adult Patients with Severe and Moderate Atopic Dermatitis," PLOS ONE, DOI: 10.1371/journal.pone.0156077, May 26, 2016, 15 pages.
Paternoster et al., "Multi-ancestry genome-wide association study of 21,000 cases and 95,000 controls identifies new risk loci for atopic dermatitis," Nature Genetics, vol. 47 (12), Dec. 2015, 10 pages.
Masashi Amano, et al., Relationship between atopic dermatitis and serum TARC level, Tenri Medical Bulletin, vol. 13 (1): 39-47 (2010).
Notice of Reasons for Rejection for JP Application No. 2021-12356, Mailing No. 083985, mailed Sep. 17, 2024.
Yamamoto, Nobuharu et al., Effect of a novel NK1 receptor antagonist, fosaprepitant (Proemend®), used in patients with oral cancer treated with cisplatin, Oral Tumors 25(3): 109-114 (2013).
Folia Pharmacol. Jpn. (Nippon Yakurigaku Zasshi) 114, Suppl 1, 209P-214P (1999).
Director of New Drugs Division, Pharmaceutical Affairs Bureau, Ministry of Health and Welfare, General Guidelines for Clinical Evaluation of New Drugs, No. 43, addressed to the Chiefs of Health Administration Departments in each prefecture (Jun. 29, 1992).
Mediaty, A et al. "Total and specific serum IgE decreases with age in patients with allergic rhinitis, asthma and insect allergy but not in patients with atopic dermatitis." Immunity & Ageing, 2005, 2 (1):9, doi:10.1186/1742-4933-2-9.
Camilleri, M. et al., Gastroparesis, Nature Reviews: Disease Primers, Article Citation ID: (2018) 4:41; pp. 1-20 (Nov. 1, 2018).

(56) References Cited

OTHER PUBLICATIONS

"Record History | ver. 2: Nov. 13, 2019 | NCT04140695 | ClinicalTrials.gov", Evaluating the Effects of Tradipitant vs. Placebo in Atopic Dermatitis (EPIONE 2), Version 2, available at https://www.clinicaltrials.gov/study/NCT04140695?cond=Atopic%20Dermatitis&intr=tradipitant&rank=1&tab=history&a=2 (Version 2 update Nov. 13, 2019).

Miller, G. "Tackling Alcoholism With Drugs." Science, Apr. 11, 2008, vol. 320, No. 5873, pp. 168-170.

Sinha, R. et al. "Translational and reverse translational research on the role of stress in drugs craving and relapse." Psychopharmacology, Apr. 15, 2011, vol. 218, No. 1, pp. 69-82.

Michael R. Ardern-Jones, Characterization of atopic dermatitis (AD) endotypes and novel treatment targets: towards a molecular classification, Experimental Dermatology, 27:433-434 (2018).

* cited by examiner

FIG. 1: WI-NRS Change by Week
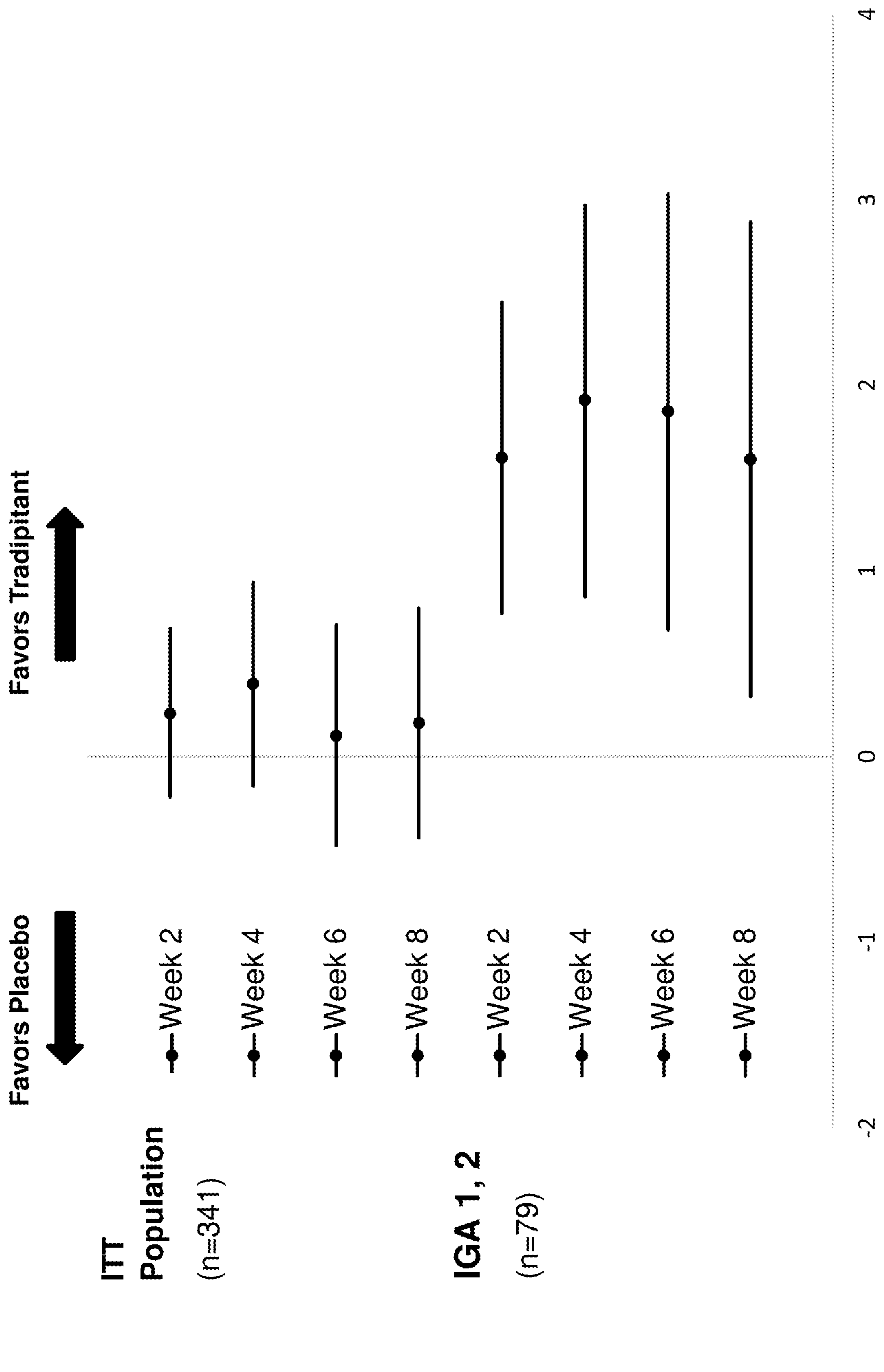

FIGS. 2A-D2: EPIONE Baseline Population

FIG. 3A
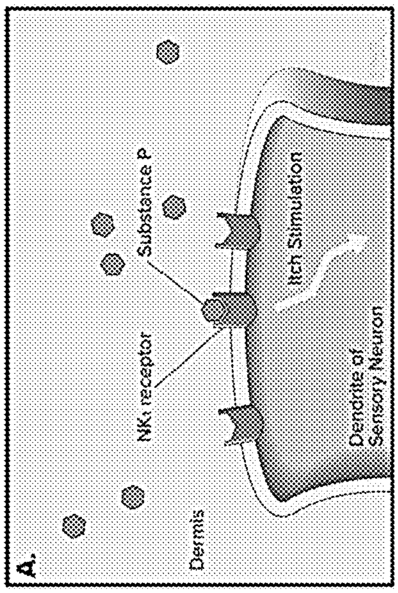
Substance P binds to $NK_1$ receptor and stimulates itch
FIG. 3B
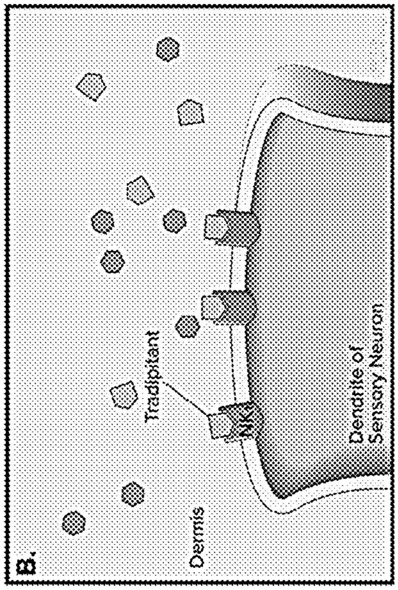
Tradipitant binds to $NK_1$ receptor, blocking substance P and inhibiting itch sensation
FIG. 3C – Mild AD
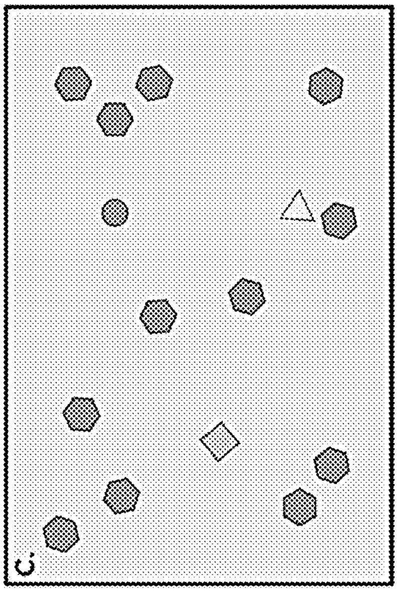
Substance P is the predominant pruritic factor in cases of mild atopic dermatitis
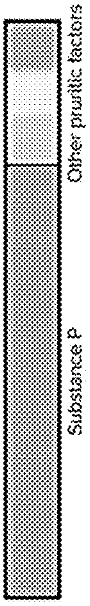
FIG. 3D – Moderate/Severe AD
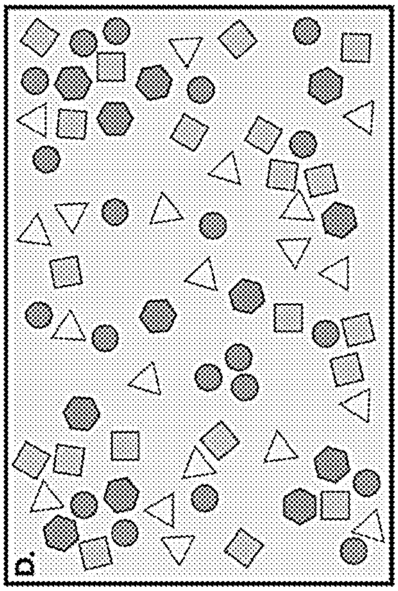
In cases of moderate or severe atopic dermatitis other pruritic factors predominate
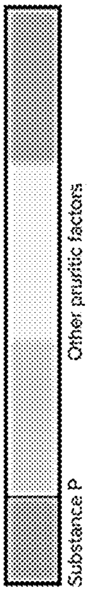

TREATMENT OF ATOPIC DERMATITIS WITH TRADIPITANT

CROSS REFERENCE TO RELATED APPLICATIONS

The present application is a US national stage application under 35 U.S.C. § 371 of international patent application no. PCT/US2021/019376, filed Feb. 24, 2021, which claims the benefit of U.S. Provisional Application No. 62/981,481, filed Feb. 25, 2020, which is incorporated by reference as though fully set forth herein.

BACKGROUND OF THE INVENTION

The invention relates generally to improvements in the treatment of pruritus, atopic dermatitis (AD), and associated symptoms with tradipitant, and more particularly, to a method for increasing the likelihood of achieving optimal therapeutic response in the treatment of an AD patient, where the AD patient is one for whom a potential therapy of choice may include the administration of an amount of tradipitant effective to treat the patient's AD.

Atopic dermatitis is a common, chronic, and relapsing inflammatory skin disorder caused by a hypersensitivity reaction in the skin, and characterized by the symptom of intense and persistent pruritus or itch, which may be localized or even generalized, and may not be relieved by scratching. The American Academy of Dermatology (AAD)'s atopic dermatitis guidelines list pruritus as an essential feature of atopic dermatitis. Other clinical features include erythema, excoriation, edema, lichenification, oozing, and xerosis. Scratching due to the itching may contribute to raw, sensitive, swollen skin, and render skin susceptible to infection. AD is also known as atopic eczema or eczema, and frequently presents during childhood.

Within the population of atopic dermatitis sufferers, the severity of individual patients' diseases span a spectrum from mild to severe. The severity of an individual patient's AD disease can be assessed and quantified using a number of different measures such as, e.g., Investigator's Global Assessment (IGA), a 100 mm unit Visual Analog Scale (VAS) for itch, Verbal Rating Scale (VRS), Dermatology Life Quality Index (DLQI), Clinical Global Impression of Change (CGI-C), Patient Benefit Index (PBI), objective and subjective SCORing Atopic Dermatitis Index (SCORAD), SKINDEX-16, Eczema Area and Severity Index (EASI) and Patient Global Impression of Change (PGIC) scale with respect to both itch and AD, and other measures of symptom severity and atopic dermatitis disease severity.

Mild and moderate to severe AD appear to be distinct entities with different presentations and courses. According to epidemiological studies, mild AD is the most common type of AD, affecting approximately 60% of the 12 million people in the US with AD. Despite classification as "mild," the milder forms of AD are nonetheless characterized by pruritus that is significant and in some cases severe. Compared with severe AD, mild AD presents with fewer lesions with mild erythema and minimal induration/papulation or oozing/crusting that are typically remitting and relapsing. Patients having an IGA score of 1 or 2 may be considered to have mild AD. Mild AD is currently treated with skin hygiene, local emollients, antihistamines, local steroids, calcineurin inhibitors, and cAMP-specific 3',5'-cyclic phosphodiesterase 4 (PDE4) inhibitors such as crisaborole. However, a significant unmet need remains for the treatment of pruritus, which may be severe, in mild AD patients.

Severe AD presents with a larger number of erythematous lesions associated with significant induration/papulation or oozing/crusting and a chronic course. Patients having an IGA score of 3 or 4 may be considered to have moderate to severe AD. Severe AD may be treated with topical regimens, phototherapy, and immunomodulating medications.

The significant pruritus, associated worsening of lesions through scratching, and sleep disruption associated with mild AD continue to represent a significant unmet medical need. A well tolerated, systemic, antipruritic agent with a strong and rapid action would provide significant value to patients, and would likely take a primary place in the treatment algorithm where AAD treatment guidelines currently indicate and recommend immunomodulating medications only for moderate to severe AD, and only after topical regimens and phototherapy are found not to adequately control the disease.

The pruritic sensation may be induced at least in part through the action of the endogenous neuropeptide substance P (SP), through the binding at neurokinin-1 (NK-1) receptors expressed on multiple skin cells. The NK-1R is expressed throughout different tissues of the body, with major activity found in neuronal tissue. SP and NK-1R interactions in neuronal tissue regulate neurogenic inflammation locally and the pain perception pathway through the central nervous system. Other tissues, including endothelial cells and immune cells, have also exhibited SP and NK-1R activity. The activation of NK-1R by the natural ligand SP is involved in numerous physiological processes, including the perception of pain, behavioral stressors, cravings, and the processes of nausea and vomiting. An inappropriate over-expression of SP either in nervous tissue or peripherally could result in pathological conditions such as substance dependence, anxiety, nausea/vomiting, and pruritus. An NK-1R antagonist may possess the ability to reduce this over-stimulation of the NK-1R, and as a result address the underlying pathophysiology of the symptoms in these conditions. NK-1 antagonists include, inter alia, aprepitant, casopitant, ezlopitant, fosaprepitant, netupitant, rolapitant, serlopitant, tradipitant, vestipitant, and vofopitant.

Tradipitant is a highly potent, selective, centrally penetrating, and orally active NK-1 receptor antagonist, with structure shown below as Formula I:

(I)

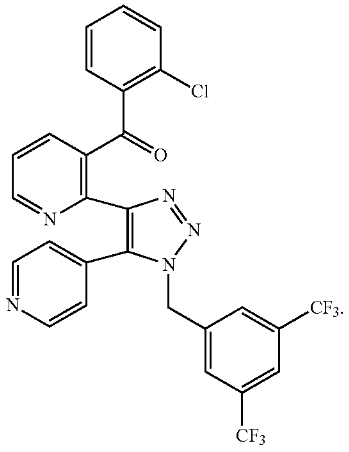

Tradipitant is disclosed in U.S. Pat. No. 7,320,994, and contains six main structural components: the 3,5-bis-trifluoromethylphenyl moiety, two pyridine rings, the triazol ring, the chlorophenyl ring, and the methanone. Tradipitant is known by the chemical names, 2-[1-[[3,5-bis(trifluoromethyl)phenyl]methyl]-5-(4-pyridinyl)-1H-1,2,3-triazol-4-yl]-3-pyridinyl](2-chlorophenyl)-methanone, and {2-[1-(3,5-bistrifluoromethylbenzyl)-5-pyridin-4-yl-1H-[1,2,3]triazol-4-yl]-pyridin-3-yl}-(2-chlorophenyl)-methanone, and has also been known as LY686017 and as VLY-686. U.S. Pat. No. 7,320,994 describes methods for using compounds, such as tradipitant, for treating a condition associated with an excess of tachykinins, most particularly where the conditions associated with an excess of tachykinins are depression and anxiety.

U.S. Pat. No. 7,320,994 further describes the use of compounds such as tradipitant in other such diseases, i.e., because these compounds inhibit the physiological effects associated with an excess of tachykinins. The patent describes the usefulness of such compounds in the treatment of numerous other disorders related to tachykinin receptor activation including psychosis, schizophrenia, and other psychotic disorders; neurodegenerative disorders such as dementia, including senile dementia of the Alzheimer's type, Alzheimer's disease, AIDS-associated dementia, and Down syndrome; demyelinating diseases such as multiple sclerosis and amyotrophic lateral sclerosis and other neuropathological disorders, such as peripheral neuropathy, diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculoskeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthyrnic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyper-reflexia and incontinence; atherosclerosis; fibrosin and collagen diseases such as scleroderma and eosinophilic fascioliasis; irritative symptoms of benign prostatic hypertrophy; disorders associated with blood pressure, such as hypertension; or disorders of blood flow caused by vasodilation and vasospastic diseases, such as angina, migraine, and Reynaud's disease; emesis, including chemotherapy-induced nausea and emesis; and pain or nociception, for example, that attributable to or associated with any of the foregoing conditions. Finally, the patent describes such compounds are effective in amounts expected to vary from about 0.001 mg/kg/day to about 100 mg/kg/day.

Tradipitant is known to be therapeutically administered through a variety of routes of administration by which it is bioavailable. U.S. Pat. No. 7,320,994 discloses administration of tradipitant by oral and parenteral routes, e.g., orally, by inhalation, subcutaneously, intramuscularly, intravenously, transdermally, intranasally, rectally, occularly, topically, sublingually, and buccally, with oral administration being generally preferred for treatment. Additionally, use of tradipitant in the treatment of pruritus and atopic dermatitis is disclosed in international patent application publication WO 2016/141341. Tradipitant is found to be safe and well-tolerated.

Treating patients with medicines typically requires a physician to determine the likelihood that a patient will respond to treatment and the extent of the therapeutic benefit that the prescribed medicine is likely to provide. Several factors can be relevant to the prescribing decision, including the patient's medical history and the severity of the patient's symptoms. For some medicines, a specific diagnostic test can provide a predicate for identifying patients that can expect to benefit from a particular medicine. Such companion diagnostic tests may serve to exclude patients from treatment with a medicine where the test indicates little or no prospect of a significant therapeutic response. In this regard, the US Food and Drug administration guidance states that companion diagnostics can identify patients who are most likely to benefit from a particular therapeutic product, https://www.fda.gov/medicaldevices/productsand medical-procedures/invitrodiagnostics/ucm407297.htm.

SUMMARY OF THE INVENTION

In an aspect of the present invention, a method is provided for increasing the probability of achieving an optimal therapeutic response in the treatment of an atopic dermatitis (AD) patient. In various embodiments, the patient may be one for whom administering an amount of an NK-1 antagonist effective to treat atopic dermatitis might be the therapy of choice. In particular, the NK-1 antagonist may be tradipitant or a pharmaceutically acceptable salt thereof, and may particularly be tradipitant, form IV or form V as described in U.S. Pat. No. 7,381,826.

The method includes examining the patient in a manner sufficient to assess the severity of the patient's AD disease, where mild AD is indicated by, inter alia, an IGA score of 1 or 2, and/or a BSA score of 10% or less. An IGA score of 3 or 4 and/or a BSA score of greater than 10% indicates non-mild AD, i.e., moderate to severe AD. If the patient is determined to have mild AD based on, inter alia, IGA and/or BSA score, the method includes prescribing an NK-1 antagonist such as tradipitant for use by the patient in an amount effective to treat said patient's AD. The effective amount of tradipitant is then administered to said patient. The amount effective to treat said patient's AD may be 100-400 mg/day, 150-400 mg/day, 100-300 mg/day, 150-300 mg/day, 100-200 mg/day, 170-340 mg/day, or 170-255 mg/day of tradipitant. In certain embodiments, the amount may be 170 mg/day of tradipitant, and may be dosed as 85 mg twice daily (bid). If the patient is not prescribed the NK-1 antagonist, e.g. tradipitant, based upon, inter alia, the patient's IGA or BSA score, the method includes evaluating whether (1) an alternative medicinal therapy other than the NK-1 antagonist, e.g. tradipitant, or (2) the use of an NK-1 antagonist, e.g. tradipitant, is nonetheless the more appropriate medical intervention for treating the patient.

These and other aspects, advantages and salient features of the invention will become apparent from the following detailed description and figures, which disclose embodiments of the invention.

BRIEF DESCRIPTION OF THE DRAWINGS

FIG. 1 illustrates change in Worst Itch-Numerical Rating Scale (WI-NRS) by week in the EPIONE study described in the Example herein.

5

Figure 2A:
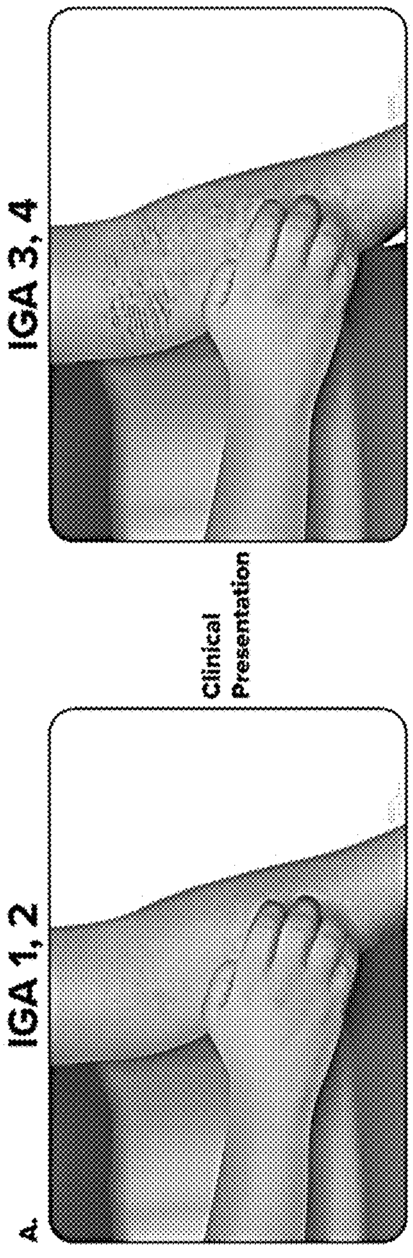
Figure 2B:
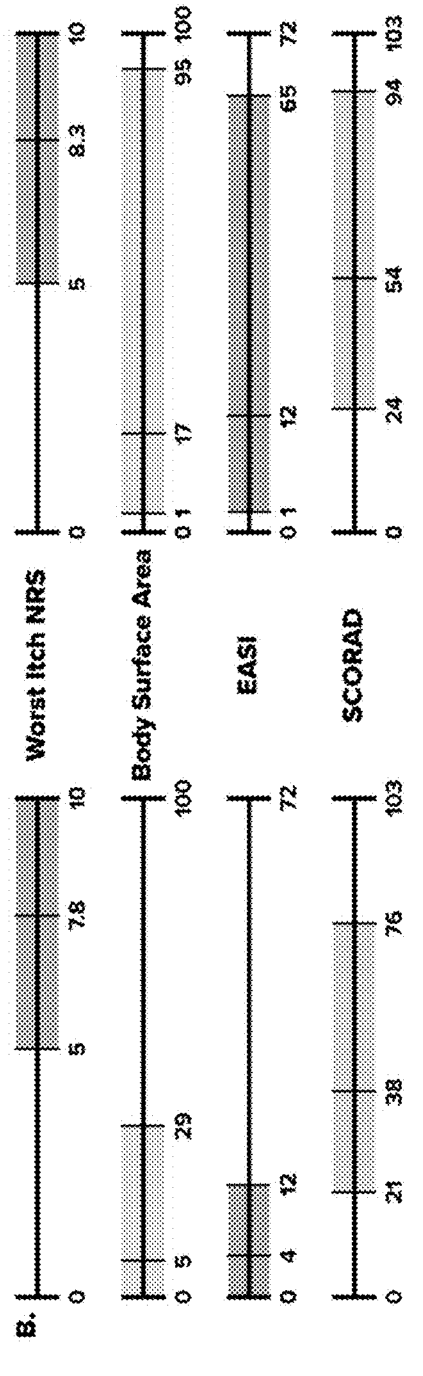
Figure 2C:
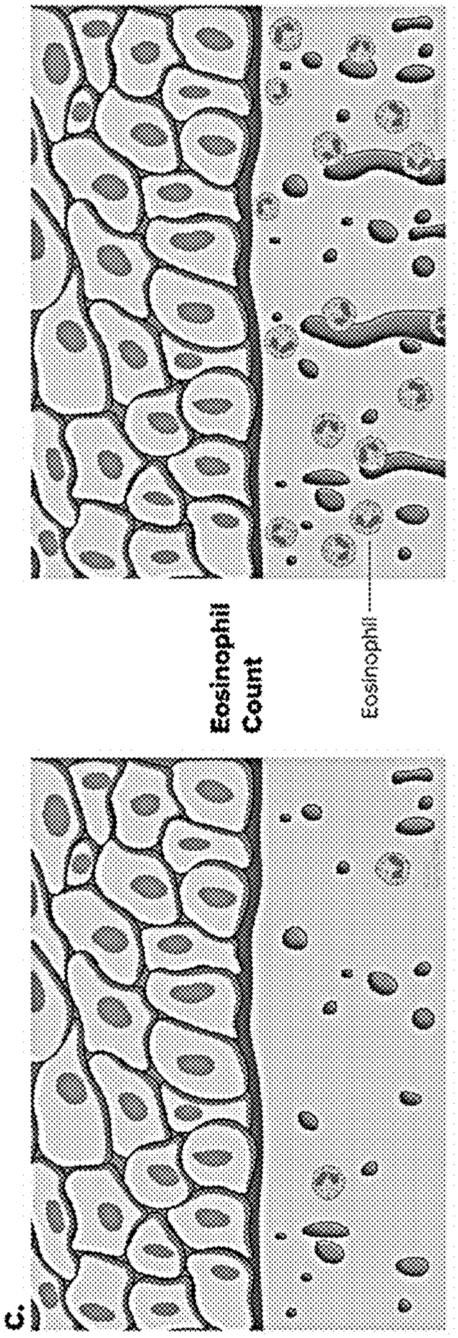
Figure 2D:
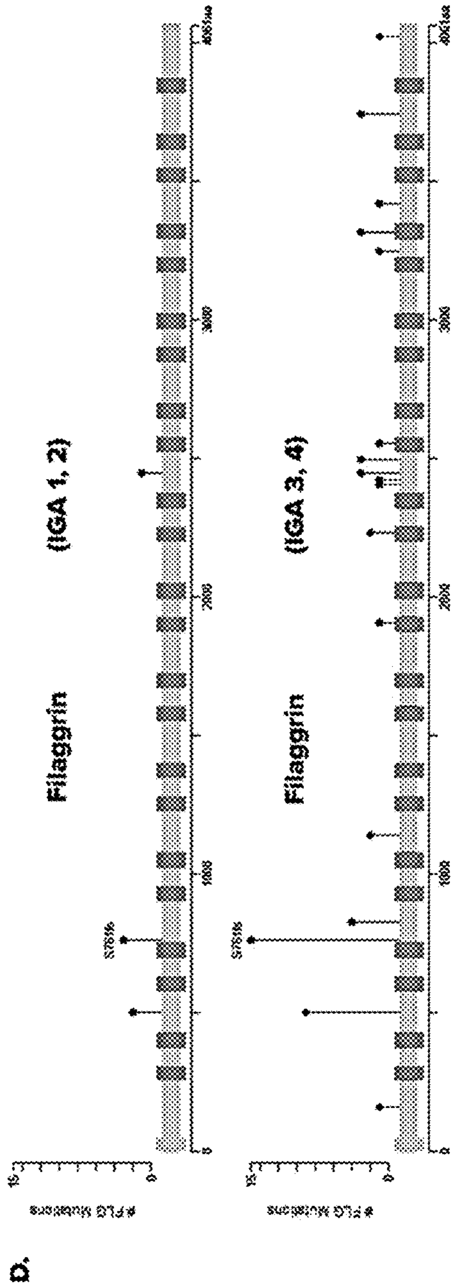

FIGS. 2A-2D illustrate baseline attributes of the study population in the EPIONE study described in the Example herein. In particular, FIG. 2A shows distinct endotypes and clinical presentation of AD as defined by IGA 1 and 2 (mild) and IGA 3 and 4 (moderate and severe). FIG. 2B shows distribution of clinical variables across endotypes as defined by IGA 1 and 2 (mild) and IGA 3 and 4 (moderate and severe). FIG. 2C shows significant differences in Eosinophil counts across endotypes as defined by IGA 1 and 2 (mild) and IGA 3 and 4 (moderate and severe). FIG. 2D shows lollipop plots displaying the location and frequency of the identified variants in Filaggrin (FLG) A significant enrichment of rare LOF variants is observed in FLG in IGA 3 and 4 AD patients (moderate and severe) as compared to IGA 1 and 2 AD patients (mild).

FIGS. 3A-3D illustrate the role of substance Pin the mediation of itch. Pruritus-related mechanisms comprise interleukins as well as neuropeptides that are relevant to neurogenic inflammation such as substance P and the pruritogen-keratinocyte communication. In the mild AD population (FIG. 3C), relatively fewer itch mediation factors including cytokines, serotonin, histamine, and eosinophils are present, leaving substance P as the predominant factor in itch. In contrast, in the more severe AD population (FIG. 3D), there are increasingly multiple factors other than Substance P involved in the cause of itch.

The drawings are intended to depict only typical aspects of the disclosure, and therefore should not be considered as limiting the scope of the disclosure.

DETAILED DESCRIPTION

In various embodiments of the invention, the methods described herein include methods for increasing the probability of achieving an optimal therapeutic response in the treatment of a patient suffering from atopic dermatitis (AD), and particularly, where the patient is one for whom administration of an effective amount of an NK-1 antagonist may be a therapy of choice to treat the AD. NK-1 antagonists are known in the art to include, e.g., aprepitant, casopitant, ezlopitant, fosaprepitant, netupitant, rolapitant, serlopitant, tradipitant, vestipitant, and vofopitant. In certain embodiments and examples described herein, the NK-1 antagonist may particularly be tradipitant. However, it is recognized that one skilled in the art may affect the patient's pruritus and/or AD by treating the patient in the manner described with an NK-1 antagonist other than tradipitant.

In one such method for increasing the probability of achieving optimal therapeutic response in the treatment of an AD patient, a provider first identifies a patient with reported pruritus associated with one or more skin lesions. "Provider" as used herein may refer to a healthcare provider, e.g., a physician, other healthcare practitioner, or licensed prescriber of medications. The provider may examine or evaluate the clinical presentation of the patient to confirm the diagnosis of AD and pruritus associated therewith, and to determine the severity of the pruritus and of the underlying AD.

In particular, the provider may identify the type of AD based on the appearance and extent of the skin lesions, and may characterize the physical appearance of the lesions using any of a number of diagnostic tools and criteria. Examples of such diagnostic tools and criteria include, for example, Investigator's Global Assessment (IGA), a 100 mm unit Visual Analog Scale (VAS) for itch, Verbal Rating Scale (VRS), Dermatology Life Quality Index (DLQI), Clinical Global Impression of Change (CGI-C), Patient

6

Benefit Index (PBI), objective and subjective SCORing Atopic Dermatitis Index (SCORAD), SKINDEX-16, Eczema Area and Severity Index (EASI) and Patient Global Impression of Change (PGIC) scale with respect to both itch and AD, and other measures of symptom severity and atopic dermatitis disease severity as known in the art. The provider may further assess and determine the patient's body surface area (BSA) affected by AD, which is provided as a percentage. These factors may be used to determine whether the patient suffers from mild, moderate, or severe AD.

In particular, IGA, BSA, or IGA and BSA may be used to determine severity of AD disease. Patients having an IGA score of 1 or 2, a BSA of less than or equal to (<) 10%, or both of an IGA or 1 or 2 and a BSA of <10% may be identified as having mild AD. Patients having an IGA score of 3 or 4, a BSA of greater than 10%, or both of an IGA score of 3 or 4 and a BSA of greater than 10%, may be determined to have moderate to severe AD.

In other embodiments, other assessments may also be used, either alone or in combination with one another or with IGA, BSA, or a combination of any of the foregoing, to determine and/or confirm the severity of AD. In particular, the provider may evaluate biochemical and genetic markers to determine whether the patient suffers, or has the propensity to suffer, from mild AD. For example, in one embodiment the provider may perform, or requisition to be performed, a diagnostic test to assess the patient's eosinophil blood count. This may be done by performance of, e.g., a complete blood count (CBC), white blood cell differential, or absolute eosinophil count. Any of the foregoing may be performed on a biological sample, e.g., blood sample, collected from the patient to be treated. An eosinophil count that is within normal reference limits may be associated with mild AD (FIG. 2C).

In another embodiment, the provider may perform a genotyping assay on a biological sample collected from the patient to be treated to identify genetic variants, e.g., in the filaggrin (FLG) gene. FLG is a member of the S100 fused type protein (SFTP family), and is located on chromosome 1 q21. FLG encodes the filaggrin protein, a skin barrier structural protein. The biological sample may include, e.g., blood, serum, saliva, urine, et al. as known in the art. The accumulation of mutations in the patient's FLG gene is associated with non-mild, e.g., moderate to severe AD disease severity in the patient, while the non-accumulation of mutations in the patient's FLG gene is associated with mild AD disease in the patient (FIG. 2D).

Using the foregoing indicia of severity, e.g., one or more of an IGA score of 1 or 2 or a BSA score of <10%, and associated biomarkers including relatively low eosinophil count, FLG genotype, and other measures, patients can be identified as suffering from mild AD or non-mild (i.e. moderate to severe) AD. As described in the Example herein, patients suffering from mild AD are more likely to experience response to treatment with tradipitant than patients with non-mild AD.

If the patient is determined to suffer from pruritus associated with mild AD, based on IGA score, BSA score, and/or other indicia described herein, an NK-1 antagonist, e.g., tradipitant may be prescribed for use by the patient, in an amount effective to treat said patient's atopic dermatitis. In various embodiments, the amount of tradipitant effective to treat the patient's pruritus or atopic dermatitis may be, e.g., 100-400 mg/day, 150-400 mg/day, 100-300 mg/day, 150-300 mg/day, 100-200 mg/day, 170-340 mg/day, or 170-255 mg/day. In certain embodiments, the amount may be 170 mg/day, and may be dosed as 85 mg twice daily (bid). The NK-1 antagonist, e.g., tradipitant may subsequently be administered in such an amount to the patient to treat the patient's pruritus and/or underlying AD. The antipruritic effect may be seen immediately after the first full day of tradipitant dosing, along with significant improvement in nighttime sleep.

If the patient is not prescribed the NK-1 antagonist, e.g. tradipitant, based upon the foregoing indicia including, e.g., IGA score and BSA score, i.e. the patient is not diagnosed as suffering from mild AD, the provider may then evaluate whether (1) an alternative medicinal therapy other than the NK-1 antagonist, e.g. tradipitant, or (2) the use of the NK-1 antagonist, e.g. tradipitant, is the more appropriate medical intervention for treating that particular patient. In the event of case (1), more appropriate treatment options are selected from those known in the art. Examples of such alternatives can be found at https://www.mayoclinic.org/diseases-conditions/atopic-dermatitis-eczema/diagnosis-treatment/drc-20353279 and include topical medicines (e.g., a corticosteroid cream or ointment, a calcineurin inhibitor, or antibiotic cream or ointments) and systemic medicines (e.g., oral corticosteroids, including prednisone or injectable preparations such as dupilumab).

Depending on the determination, an alternative medical therapy may be administered, or the NK-1 antagonist, e.g. tradipitant may be administered. In the case that tradipitant is administered to the patient, but not on the basis of IGA and/or BSA score, the patient may be monitored more closely for response to treatment, as AD patients demonstrating a response to tradipitant treatment may respond as soon as after the first full day of tradipitant dosing. The provider may monitor the patient at least through this window of time following administration to assess whether satisfactory treatment response is obtained with tradipitant.

The skilled artisan will appreciate that additional embodiments may be selected by combining the embodiments above, or by reference to the examples given herein.

Example: EPIONE Study

A randomized, placebo-controlled phase III study is conducted in atopic dermatitis (AD) patients with severe pruritus with a range of disease severity presentation from mild (23%) to moderate (64%) and severe (13%) as determined by the Investigator's Global Assessment scale (IGA). In the study, patients (n=341) are randomized 1:1 to receive either tradipitant or placebo for a treatment period of eight (8) weeks. Patients in the tradipitant arm of the study are dosed with 85 mg tradipitant twice daily (bid). Patients are assessed at baseline and post-randomization with a number of symptomatic and disease severity scales at regular intervals.

At week 8, patients in both the tradipitant and placebo arms of the study demonstrate significant and meaningful improvement in pruritus, as measured by the Worst Itch Numeric Rating Scale (WI-NRS). The tradipitant magnitude of improvement is greater than that of placebo, although the difference between treatment groups is not statistically significant.

A significant interaction is observed between baseline disease severity and treatment (p=0.0004), where disease severity is measured by Investigator's Global Assessment (IGA) on a scale of 1-4. This suggests that study participants with different baseline disease severity experience different treatment outcomes.

When accounting for baseline disease severity and treatment interaction, a significantly larger improvement in WI-NRS is seen with tradipitant compared to placebo at the pre-specified endpoint of week 8 in the full trial population (p=0.0217). Similar effects are seen throughout the treatment periods at all post-randomization visits comprising weeks 2, 4, 6 and 8 (Table 1).

TABLE 1

EPIONE Results Summary

| Endpoints[1] | Visit | Tradipitant | Placebo | Diff | P-value |
|---|---|---|---|---|---|
| WI-NRS | Week 2 | −1.68 | −1.44 | 0.23 | 0.3092 |
| ITT (n = 341) | Week 4 | −2.58 | −2.20 | 0.39 | 0.1664 |
| Tradipitant (n = 171) | Week 6 | −3.00 | −2.89 | 0.11 | 0.7105 |
| Placebo (n = 170) | Week 8 | −3.61 | −3.43 | 0.18 | 0.5667 |
| WI-NRS Adjusting for IGA Severity | Week 2 | −2.43 | −1.29 | 1.14 | 0.0069 |
| ITT (n = 341) | Week 4 | −3.34 | −2.05 | 1.29 | 0.0042 |
| | Week 6 | −3.75 | −2.74 | 1.01 | 0.0284 |
| | Week 8 | −4.36 | −3.28 | 1.08 | 0.0217 |
| WI-NRS | Week 2 | −2.59 | −0.98 | 1.61 | 0.0003 |
| IGA 1, 2 (n = 79) | Week 4 | −3.39 | −1.48 | 1.92 | 0.0005 |
| Tradipitant (n = 40) | Week 6 | −4.18 | −2.32 | 1.86 | 0.0024 |
| Placebo (n = 39) | Week 8 | −4.74 | −3.14 | 1.60 | 0.0152 |
| Diary WI–NRS | Week 2 | −1.54 | −0.36 | 1.18 | 0.0002 |
| IGA 1, 2 (n = 79) | Week 4 | −2.78 | −1.07 | 1.71 | 0.0002 |
| | Week 6 | −3.48 | −1.72 | 1.76 | 0.0011 |
| | Week 8 | −4.23 | −2.14 | 2.09 | 0.0010 |
| Responder Analysis (%)[2] (n = 79) | | | | | |
| WI-NRS ≥4 Improvement | Week 8 | 72.5 | 33.3 | 39.2 | 0.0007 |
| SCORAD 50% Improvement | Week 8 | 55.0 | 30.8 | 24.2 | 0.0411 |
| IGA 0 or 1 | Week 8 | 60.0 | 38.5 | 21.5 | 0.0729 |

[1]P-values are from MMRM analysis.

[2]P-values are from Fisher's exact test.

A subgroup analysis shows that patients with mild disease severity (23% of study patients, IGA 1, 2) experience the largest improvement over placebo. Specifically, in the mild AD group, tradipitant significantly improves WI-NRS over placebo at every visit (Table 1, FIG. 1). The categorical WI-NRS responder analysis (>4 point improvement) showed that 72.5% of tradipitant patients had a clinically meaningful response as compared to 33.3% of placebo patients.

These results suggest a large and significant antipruritic effect of tradipitant in mild AD, which is consistent with patient daily diary entries. For mild AD patients, a time course of response also shows that the antipruritic effect is seen immediately after the first full day of tradipitant dosing, suggesting a large and immediate therapeutic effect. Similar improvement is observed for nighttime sleep, which is often disrupted in patients with severe pruritus.

Additionally, results suggest that mild and non-mild (e.g. severe) AD appear to be distinct endotypes with a different set of causative factors and course. Non-mild, i.e., moderate to severe AD (IGA 3, 4) is associated with significantly higher count of eosinophils in the blood as compared to mild AD (IGA 1, 2), as shown in FIG. 2C. Eosinophils are mediators of the inflammatory response and are responsible for recruiting other immune cells in the lesions. Eosinophils are involved directly or indirectly in the production and secretion of pruritogenic and inflammatory mediators including histamine, serotonin, substance P, NGF, and a number of interleukin cytokines. As such, it is likely that severe pruritus associated with mild and severe AD may have different mediators. (FIGS. 3A-3D).

Further, whole genome sequence analysis (WGAS) shows that particular genetic markers are associated with mild AD vs. non-mild (i.e. moderate to severe) AD. For example, the accumulation of rare loss of function (LOF) mutations in the patient's filaggrin (FLG) gene is associated with non-mild (e.g. moderate to severe) AD disease severity in the patient, while non-accumulation of mutations in the patient's FLG gene is associated with mild AD disease in the patient (FIG. 2D).

Tradipitant appears to produce a large and rapid antipruritic effect in mild AD, providing a significant and immediate onset of itch reduction by the first full day of treatment while having a relatively safe profile. This may provide a much-needed therapy for the majority of AD patients that experience mild AD lesion severity but still suffer from significant pruritus.

The foregoing description of various aspects of the invention has been presented for purposes of illustration and description. It is not intended to be exhaustive or to limit the invention to the precise form disclosed, and modifications and variations are possible. Such modifications and variations that may be apparent to a person skilled in the art are intended to be included within the scope of the invention as defined by the accompanying claims.

We claim:

1. A method comprising:

selecting for treatment an individual suffering from atopic dermatitis, wherein the individual is selected for treatment by:

examining the individual in a manner sufficient to assess a severity or an extent of the atopic dermatitis;

determining that the individual suffers from atopic dermatitis of mild severity or extent; and orally administering tradipitant to the selected individual in an amount effective to treat the atopic dermatitis.

2. The method of claim 1, wherein the amount of tradipitant effective to treat the atopic dermatitis is about 170 mg/day.

3. The method of claim 2, wherein the amount of tradipitant effective to treat the atopic dermatitis is 170 mg/day given as 85 mg twice daily (bid).

4. The method of claim 1, wherein the amount of tradipitant effective to treat the atopic dermatitis is 100-400 mg/day.

5. The method of claim 4, wherein the amount of tradipitant effective to treat the atopic dermatitis is 100-300 mg/day.

6. The method of claim 5, wherein the amount of tradipitant effective to treat the atopic dermatitis is 100-200 mg/day.

7. The method of claim 4, wherein the amount of tradipitant effective to treat the atopic dermatitis is 170-340 mg/day.

8. The method of claim 7, wherein the amount of tradipitant effective to treat the atopic dermatitis is 170-255 mg/day.

9. The method of claim 1, wherein the atopic dermatitis of mild severity or extent is characterized by an Investigator's Global Assessment (IGA) score corresponding to a score of 1 or 2 out of 4.

10. The method of claim 1, wherein the atopic dermatitis of mild severity or extent is characterized by a body surface area (BSA) score of 10% or less.

11. A method of treating atopic dermatitis in an individual in need thereof, comprising:

orally administering to the individual tradipitant at a dose of 100-400 mg/day in a solid immediate release form, wherein the individual suffers from atopic dermatitis of mild severity or extent.

12. The method of claim 11, wherein the atopic dermatitis of mild severity or extent is represented by an Investigator's Global Assessment (IGA) score corresponding to a score of 2 or less on a scale of 1-4.

13. The method of claim 12, wherein the atopic dermatitis of mild severity or extent is represented by an IGA score corresponding to a score of 1 or 2 on a scale of 1-4.

14. The method of claim 11, wherein the atopic dermatitis of mild severity or extent is represented by a body surface area (BSA) score of 10% or less.

15. The method of claim 11, wherein the dose of tradipitant comprises 100-300 mg/day.

16. The method of claim 15, wherein the dose of tradipitant comprises 100-200 mg/day.

17. The method of claim 16, wherein the dose of tradipitant comprises 170 mg/day.

18. The method of claim 17, wherein the dose of tradipitant comprises 170 mg/day, given as 85 mg twice daily (bid).

19. The method of claim 11, wherein the dose of tradipitant comprises 170-340 mg/day.

20. The method of claim 19, wherein the dose of tradipitant comprises 170-255 mg/day.

* * * * *